United States Patent
Slobodan et al.

(12)

(10) Patent No.: US 10,488,338 B2
(45) Date of Patent: Nov. 26, 2019

(54) METHODS FOR ASSESSING FRAGMENT LENGTHS OF MOLECULAR CHAINS USING MULTIPLE DYES

(71) Applicant: COASTAL GENOMICS INC., Burnaby (CA)

(72) Inventors: Jared Slobodan, Richmond (CA); Matthew Nesbitt, Langley (CA)

(73) Assignee: Coastal Genomics Inc., Burnaby, British Columbia (CA)

( * ) Notice: Subject to any disclaimer, the term of this patent is extended or adjusted under 35 U.S.C. 154(b) by 0 days.

(21) Appl. No.: 14/895,074

(22) PCT Filed: Jun. 11, 2014

(86) PCT No.: PCT/US2014/042019
§ 371 (c)(1),
(2) Date: Dec. 1, 2015

(87) PCT Pub. No.: WO2015/023351
PCT Pub. Date: Feb. 19, 2015

(65) Prior Publication Data
US 2016/0123883 A1 May 5, 2016

Related U.S. Application Data

(60) Provisional application No. 61/833,823, filed on Jun. 11, 2013.

(51) Int. Cl.
*G01N 21/64* (2006.01)
*G01N 27/447* (2006.01)

(52) U.S. Cl.
CPC ..... *G01N 21/6428* (2013.01); *G01N 21/6486* (2013.01); *G01N 27/44726* (2013.01); *G01N 2021/6441* (2013.01)

(58) Field of Classification Search
None
See application file for complete search history.

(56) References Cited

U.S. PATENT DOCUMENTS

| 5,783,687 A | 7/1998 | Glazer et al. |
| 2003/0013159 A1* | 1/2003 | Cohen ............... C07K 14/47 435/69.1 |
| 2003/0082618 A1* | 5/2003 | Li ....................... C12Q 1/6809 435/6.16 |
| 2010/0099082 A1* | 4/2010 | Lion ................... C12Q 1/6858 435/6.11 |

FOREIGN PATENT DOCUMENTS

| EP | 1813938 A1 | 8/2007 |
| EP | 2105736 A1 | 9/2009 |
| EP | 2113574 A1 | 11/2009 |

OTHER PUBLICATIONS

Diwan et al., "Automated sizing of fluorescent-labeled simple sequence repeat (SSR) markers to assay genetic variation in soybean", Theor. Appl. Genet., vol. 95, pp. 723-733. (Year: 1997).*
Mueller, Odilo, "High precision restriction fragment sizing with the Agilent 2100 Bioanalyzer," Agilent Technologies, publication No. 5968-7501E, pp. 1-8. (Year: 2000).*
Agilent Technologies, "Agilent DNA 7500 and 12000, Kit Guide" Agilent Technologies publication, December, pp. 1-24. (Year: 2016).*
European Patent Office, Extended European Search Report, EP 14836664.4, dated Dec. 16, 2016.
International Search Report and Written Opinion dated Nov. 25, 2014 in connection with PCT/US2014/042019.

* cited by examiner

*Primary Examiner* — Young J Kim
(74) *Attorney, Agent, or Firm* — Quarles & Brady LLP

(57) ABSTRACT

A method for visualizing and discriminating between DNA/RNA fragment(s) of unknown length(s) and an internal marker(s) of known length in a sample that is disposed in a common electrophoresis gel laneway. The method comprises labeling the DNA/RNA fragment(s) with a first dye and labeling the internal marker(s) with a second dye. The first and second dyes have discrete fluorescent emission spectra, which may be used to visually discriminate the DNA/RNA fragment(s) and the internal marker(s).

8 Claims, 3 Drawing Sheets

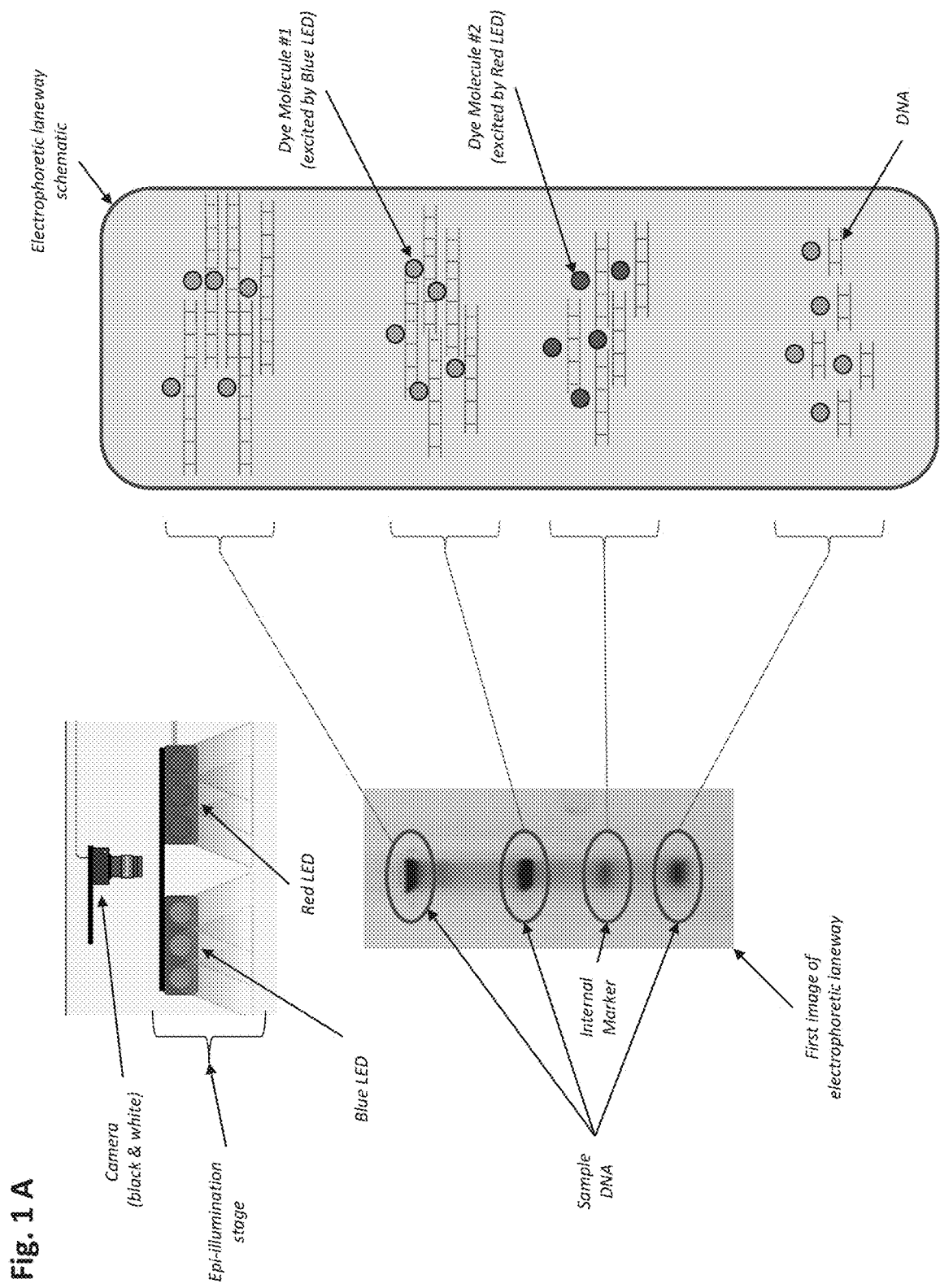

METHODS FOR ASSESSING FRAGMENT LENGTHS OF MOLECULAR CHAINS USING MULTIPLE DYES

CROSS-REFERENCE TO RELATED APPLICATIONS

Figure 1B:
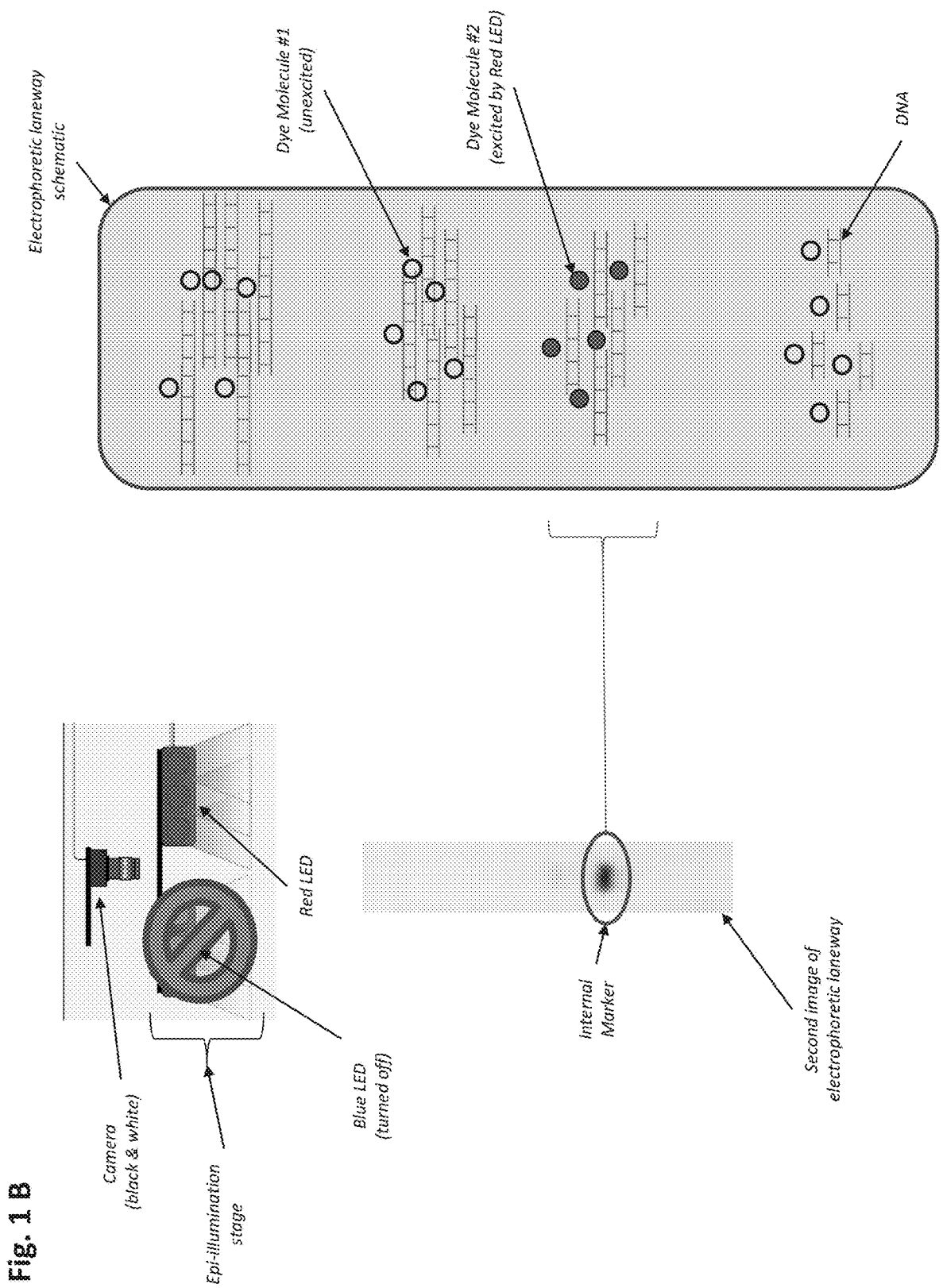

This application represents the national stage entry of PCT International Application No. PCT/US2014/042019 filed Jun. 11, 2014, which claims priority of U.S. Provisional Patent Application No. 61/833,823 filed Jun. 11, 2013, the disclosures of which are incorporated by reference here in their entirety for all purposes.

BACKGROUND

Electrophoretic separation of nucleic acid (DNA/RNA) strands based on fragment length (by means of a gel or capillary) is a widely used tool in laboratory genetics. This process is used to assess the distribution of fragment lengths in a DNA/RNA sample. Visualization of DNA/RNA after electrophoretic separation relies on the attachment of one or more dye molecules to the DNA/RNA. A dye molecule can be excited to fluorescence in order to ascertain the location of DNA/RNA within a gel column, channel or other laneway (hereinafter collectively "laneway" unless otherwise presented) along which the DNA/RNA has traversed via electrophoresis. Interpretation of the DNA/RNA fragment length distribution generally relies upon a comparison between at least one sizing reference, and preferably a plurality of sizing references, which consist of DNA/RNA of discrete, known sizes ("markers"). The implementation of markers can come in varying forms, but a common method to optimize sizing accuracy is to include the markers in the same laneway for electrophoresis as the fragmented DNA/RNA.

One currently preferred method for estimating the size of DNA/RNA fragments using electrophoresis comprises the inclusion of known markers within a sample of such fragments before commencing electrophoresis, i.e., use of internal markers. However, as both the DNA/RNA sample and markers usually incorporate the same dye to facilitate visualization thereof within the laneway, it can be difficult or impossible to distinguish between the two if there is a significant concentration of DNA/RNA fragments of the same size and with the same length(s) as the marker(s). In such situations, the fluorescence from the dye attached to the DNA/RNA sample fragments will often mask the fluorescence of the marker(s) dye. This consequence results inaccurate size estimation of the DNA/RNA fragment lengths insofar as the internal marker(s) cannot be distinguished to provide a reference for comparison.

The problem of masking the fluorescence signal of the internal marker can be largely avoided through selection of internal markers that are of a size that permits their discrimination from the sample. The Bioanalyzer 2100 capillary electrophoresis system (Agilent Technologies), for example, utilizes a two internal marker system with one being very small (~15-50 bp) and the other being very large (~1.5-17 kbp) to automatically assess the fragment length distribution of DNA/RNA. By selecting internal markers of divergent lengths, the chances of significant overlap of fragment lengths between the sample DNA/RNA and the markers are statistically minimized.

While the use of divergent length internal markers can circumvent the masking problem described above, the results of fragment length estimation are improved when the internal marker(s) are of a size that more closely approximates that of the sample: more accurate estimations of DNA/RNA fragment lengths can be provided by using more suitably sized internal markers, however, doing so increases the likelihood of undesirable fluorescence masking.

Another approach for estimating the size of DNA/RNA fragments using electrophoresis comprises the use of external markers, i.e., introducing markers into a laneway adjacent to the laneway(s) loaded with the DNA/RNA sample(s). After electrophoresis has been completed, estimations of fragment lengths in the sample laneway(s) can be made by comparing them to the external marker laneway.

External marker fragment sizes can be suitably chosen to match the fragment size ranges of the sample; there is no chance for any overlap or fluorescence saturation between them. However, the comparison is not optimal as variances in applied current and the laneway matrix composition between the external marker(s) and the DNA/RNA samples can confound sizing approximations. Additionally, the actual sample contents can impact fragment mobility, such that the migration speed of identical molecules can differ between channels depending upon the remaining sample composition. To account for variances and improve fragment length estimations, it is best to include the markers with the DNA/RNA sample in the same laneway.

Finally, another method for assessing fragment lengths involves labeling internal markers with fluorescent dyes with unique excitation/emission spectra on the ends of DNA/RNA molecules. This method has limitations though. Because dye molecules are only attached to the ends of the internal markers, any signal emitted by such a marker molecule is minimal, and can only be detected by highly sensitive, costly detectors that are not compatible with gel electrophoresis. Additionally, large markers (i.e., larger than 2,500 bp) have exceedingly high DNA/RNA fragment/dye molecule ratios. And, because the absolute mass of markers that can be loaded has a practical upper limit, this ratio prohibits the utilization of large internal markers even for analytical systems with highly sensitive detectors (i.e., capillary systems).

SUMMARY OF THE INVENTION

Mindful of the foregoing deficiencies associated with the prior art, the instant invention is directed to methods for separately visualizing DNA/RNA samples from internal markers in a common electrophoresis laneway, to assist in estimating DNA/RNA fragment lengths within the sample. As a consequence, one or more internal markers can be selected, which may be nested within the distribution of DNA/RNA sample fragments during estimation of the fragment length distribution of a DNA/RNA sample, for maximum comparative value. Beneficially, the historical problem of internal marker fluorescence signal masking by that of the DNA/RNA fragments is eliminated, yet internal marker fluorescence signal strengths are sufficient for use even in less sensitive electrophoresis apparatus, such as those using CCD or MOSFET imaging hardware (e.g., conventional digital camera technologies) and/or non-coherent illumination hardware (e.g., conventional LED technologies).

The invention comprises the use of a plurality of fluorescing dyes for DNA/RNA sample fragments and at least one internal marker in a sample to enable concurrent fluorescence in an electrophoresis apparatus and yield non-competing emission spectra, and/or sequential fluorescence to similarly yield non-competing emission spectra but that are temporally separated.

If enhanced fragment length resolution is desired, multiple internal markers and/or dyes can be used according to the invention with respect to single dye-marker combinations. Thus, methods according to the invention include labeling of any internal marker with at least one, and preferably more than one, unique dye molecule throughout the length of the internal marker. This makes the size estimation approach compatible with low-cost detector means (e.g., an optical camera) that are often used with gel electrophoresis. It also enables the utilization of large internal markers (e.g., >~2500 bp) with the multiple dye methodology advanced herein.

In addition to increased sensitivity and fragment length selectivity, the ability to exclusively visualize an internal marker when practicing various invention embodiments obviates the need to load an absolute mass of an internal marker that otherwise would be reliably distinguishable from the fluorescence signal of the DNA/RNA of interest. Consequently, generally less than 10% of the original internal marker is necessary to achieve desired elucidation that otherwise would be necessary without use of the multiple dye solution according to the invention. Such a reduction over prior art single dye solutions is projected to save more than 50% in operating costs in addition to increasing accuracy of DNA/RNA fragment evaluation when practicing dual dye embodiments of the invention. Axiomatically, technicians are no longer required to have detailed advance knowledge of potential overabundant fragment lengths in the DNA/RNA sample that could mask the signal from selected internal markers. The multiple dye methods according to the invention will therefore also reduce the time needed to conduct fragment length distribution assessments.

In one series of invention embodiments, a first dye having a first emission spectra when fluoresced by a first excitation means, such as limited wavelength light source, is associated with at least one marker, and a second dye having a second emission spectra different from the first dye when fluoresced by a second excitation means, such as limited wavelength light source different from the first excitation means, is associated with a plurality of DNA/RNA sample fragments, wherein the DNA/RNA sample fragments and the at least one marker are disposed in a common gel electrophoresis laneway. At least a portion of the laneway is concurrently excited by the first and second excitation means such that both dyes simultaneously fluoresce, and/or the dyes are sequentially fluoresced. As a consequence of this methodology, one or more internal markers with a size that may be expected to overlap with an overly abundant fragment length (known as an adaptermer), which may be present in a DNA/RNA sample being characterized, may be selected. Such overlap, which permits high precision comparisons between the marker(s) and the DNA/RNA sample fragments finds particular utility with respect to estimations of the fragment length distributions for a set of biologically important nucleic acid molecules known as miRNAs.

A method for accomplishing the foregoing dye associations comprises covalently bonding one of the dyes to multiple sites on at least one, and preferably a plurality of, DNA/RNA sample fragments, and effecting a lesser strength bond between the other dye and multiple sites on at least one, and preferably a plurality of, marker fragments. Thus, dye molecules and compounds comprising the same such as Cy5, Alexa Fluor 647, and DyLight 650 may be used to first establish labeling of markers while dye molecules and compounds comprising the same such as SYBR Gold, SYBR Green, Ethidium Bromide, and Pico Green may be used to then establish labeling of DNA/RNA sample fragments.

It should be noted that in the example referenced above, separate association of non-covalently bonded dye molecules is not necessary. Suitable results have been obtained from simultaneous exposure of the labeled markers and the unlabeled DNR/RNA fragments to the non-covalently bonded dye molecule. While there may still be bonding sites available on the markers, the fact that the markers already have a plurality of dye molecules covalently bonded thereto minimizes available bonding sites, and the unique fluorescence signatures between the dyes enables appropriate position substitution during subsequent assay steps. Therefore and generally stated, the various invention embodiments are sufficiently enabled when at least one of the markers or the DNA/RNA sample fragments are exclusively labeled with one of the unique dyes.

In view of the increases in sensitivity, selectivity of fragment length determination, choice of DNA/RNA fragment sizes to use as internal markers, as well as the decrease in operating costs and time, the invention as exemplified in its various embodiments represents a significant advancement over prior art efforts in the field of electrophoresis in gel-type media using internal markers with dye-assisted visualization opportunities.

DETAILED DESCRIPTION OF AN INVENTION EMBODIMENT

Referring generally to FIGS. 1A and 1B, DNA/RNA is electrophoresed along a laneway (see Electrophoretic laneway schematic) causing smaller fragments to travel through the medium at a faster rate than larger fragments and thus, the sample is separated by fragment length, as is well known in the art. As both DNA/RNA and internal markers are run together, they can be visualized together during electrophoresis. In FIG. 1A, double stranded Sample DNA has been labeled with a first dye (Dye Molecule #1) and when excited by a Blue LED emits green light. Internal Marker has been labeled with a second dye (Dye Molecule #2) and when excited with a Red LED emits red light. A Camera captures a First image of the electrophoretic laneway and passes the data to a software image analysis package.

In FIG. 1B, the Blue LED is immediately turned off to extinguish excitation of Dye Molecule #1 and abrogate emission of the green light. With the Red LED still exciting Dye Molecule #2, the Internal Marker is exclusively visualized. The Camera then captures a Second image of the electrophoretic laneway and passes it to the software image analysis package. The package then compares the two images, and, knowing the size of the Internal Marker, assesses the size of the surrounding fragment lengths that constitute the Sample DNA. Note that in another embodiment of this process, the First image of the electrophoretic laneway can be captured when only the Blue LED is on to only visualize the Sample DNA. This ensures that visualization of the Internal Marker and Sample DNA can be mutually exclusive.

Figure 2:
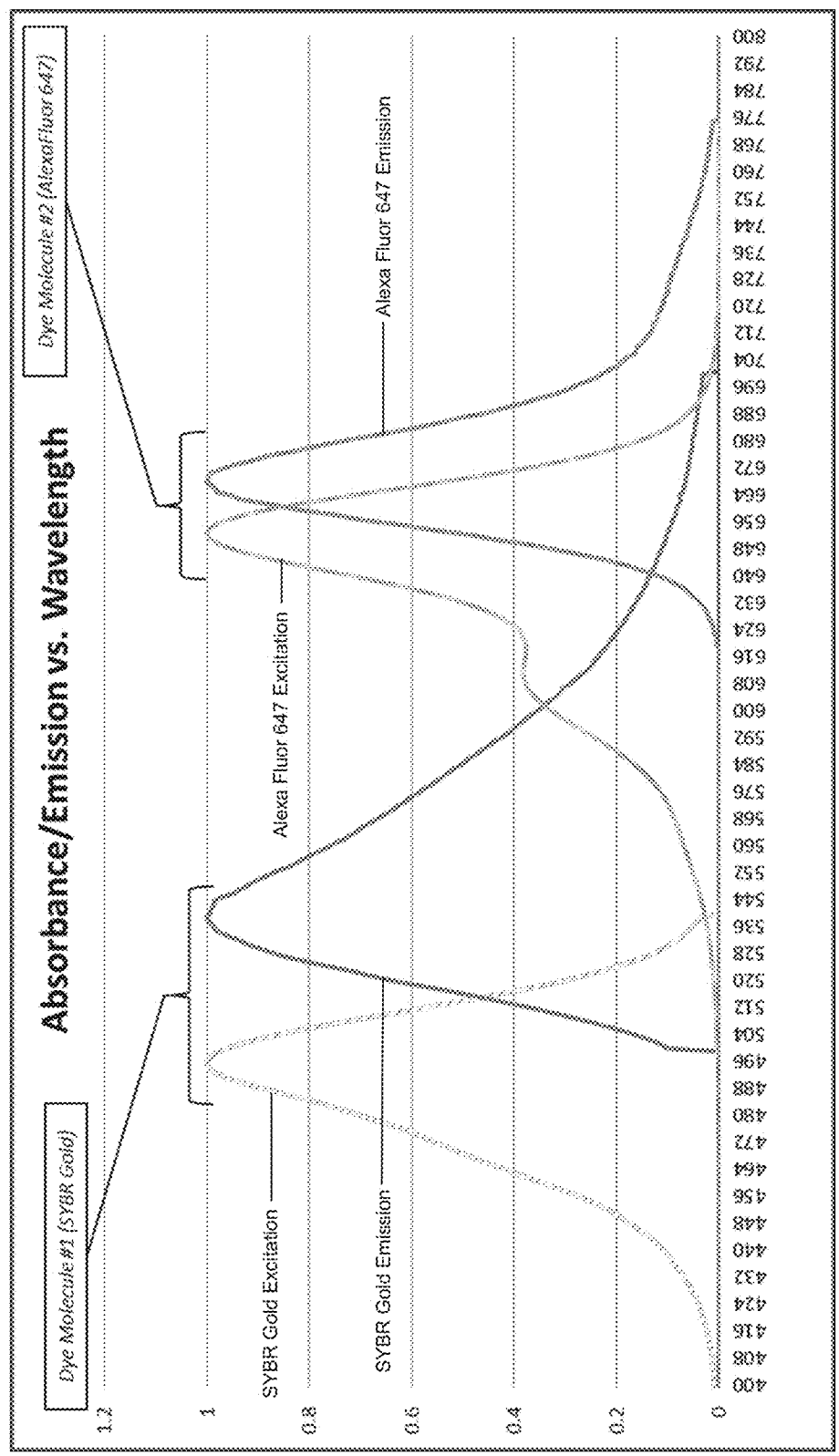

Referring next to FIG. 2, representative Excitation/Emission spectra for two candidate dye molecules that could be used in the dual dye system are shown. Dye Molecule #1 occupies an excitation/emission wavelength range that is sufficiently different from that of Dye Molecule #2 to enable discrimination between the two.

What is claimed:

1. A method for visualizing at least one DNA sample fragment or at least one RNA sample fragment separately from at least one internal marker having a length of at least 2500 base pairs and being of a known length, to assist in estimating a DNA fragment length or a RNA fragment length, where the at least one internal marker is in a common electrophoretic laneway with the at least one DNA sample fragment or the at least one RNA sample fragment, the method comprising:

labeling the at least one internal marker having a length of at least 2500 base pairs with a plurality of first dye molecules that exclusively labels the at least one internal marker throughout its length, each of the plurality of first dye molecules being the same and having a first emission spectra when fluoresced by a first excitation means;

labeling the at least one DNA sample fragment or at least one RNA sample fragment with a second dye molecule, the second dye molecule being different from the plurality of first dye molecules and having a second emission spectra when fluoresced by a second excitation means, the second emission spectra being different than the first emission spectra, exciting said laneway with said first excitation means and said second excitation means, and visualizing the at least one DNA sample fragment or at least one RNA sample fragment when fluoresced by the second excitation means, said visualizing occurring separately from the visualization of the at least one internal marker.

2. The method of claim 1, wherein the laneway is concurrently excited by the first and second excitation means.

3. The method of claim 1, wherein the laneway is sequentially excited by the first and second excitation means.

4. The method of claim 1, wherein the first dye molecule is Cy5.

5. The method of claim 1, wherein the second dye molecule is Ethidium Bromide or Cy5.

6. The method of claim 1, wherein the at least one DNA sample fragment or at least one RNA sample fragment is at least one DNA sample fragment.

7. The method of claim 1, wherein the at least one DNA sample fragment or at least one RNA sample fragment is at least one RNA sample fragment.

8. The method of claim 1, wherein the electrophoretic laneway is in a slab gel.

* * * * *